United States Patent [19]

Fox

[11] Patent Number: 4,508,568

[45] Date of Patent: Apr. 2, 1985

[54] BIOCIDAL WOOD PRESERVATIVE COMPOSITION AND METHOD

[75] Inventor: Richard C. Fox, San Rafael, Calif.

[73] Assignee: Chevron Research Company, San Francisco, Calif.

[21] Appl. No.: 373,558

[22] Filed: Apr. 30, 1982

Related U.S. Application Data

[63] Continuation-in-part of Ser. No. 200,812, Oct. 27, 1980, abandoned.

[51] Int. Cl.³ .............................................. C09D 5/20
[52] U.S. Cl. .................................... 106/2; 106/18.29; 106/270; 428/541; 428/907
[58] Field of Search ................... 106/2, 18.29, 18.35, 106/270; 428/541, 907

[56] References Cited

U.S. PATENT DOCUMENTS

| | | | |
|---|---|---|---|
| 3,061,508 | 10/1962 | Morriss et al. | 167/42 |
| 4,013,804 | 3/1977 | Gruetzman | 427/33 |
| 4,085,251 | 4/1978 | Rak | 428/485 |

*Primary Examiner*—George F. Lesmes
*Assistant Examiner*—E. Rollins Buffalow
*Attorney, Agent, or Firm*—S. R. LaPaglia; J. M. Whitney; J. J. DeYoung

[57] ABSTRACT

The invention encompasses a petrolatum wax-biocidal composition and a method of preserving wood with the composition.

12 Claims, No Drawings

BIOCIDAL WOOD PRESERVATIVE COMPOSITION AND METHOD

This application is a continuation-in-part of my co-pending application, U.S. Ser. No. 200,812, filed Oct. 27, 1980 now abandoned.

BACKGROUND OF THE INVENTION

This invention relates to wax preservative compositions. More specifically, the invention relates to a petrolatum wax-biocidal composition and a method for preserving wooden articles.

Wood and wooden articles degrade when exposed to fungus and/or high humidity environments. When wood is immersed in water the degradation is accelerated. Exposure to salt water or fresh water containing woodboring animals and/or crustaceans such as worms or barnacles and plant life such as algae and the like tend to further accelerate degradation process.

To increase the useful lifetime of wood and wooden articles, the wood can be treated with antifungicidal and biocidal compositions. The compositions usually contain paraffinic waxes, petroleum distillates, water, and one or more antifungicidal and/or biodical compounds. The wax is usually less than about 10% by weight of the composition. The wax emulsion compositions require surfactants to prevent the separation of the composition during storage. In addition, the petroleum distillates can be highly flammable so that the articles must be thoroughly dried in an open-air environment prior to use. The drying of the articles lengthens the manufacturing process and increases the cost of the final product. Furthermore, paraffin wax compositions tend to crack during thermocycling and have low enough melting points so that the preservative will tend to leach out of the wax in warm climates.

Thus, it would be highly desirable to have a composition and method of treating wooden articles with a low cost, flexible, high melting and flash point material. It would also be desirable to have a composition with a structure that provides for the time release of a biocidal or antifungicidal agent incorporated in the composition.

BRIEF SUMMARY OF THE INVENTION

The composition comprises a mixture of a biocidal compound and petrolatum wax having an oil content in excess of about 10% has a high-flash point, which can withstand thermocycling, and is low in cost. The structure of the wax also provides for the timed release of the biocidal compound. The wax can have oil added thereto or be a petroleum wax having crude oil therein. The composition can be easily applied to any object and especially wooden objects to preserve same. The composition is heated to above its congealing point and applied to the article to be treated by spraying, dipping, and the like.

The composition preserves wood and functions as an antifouling coating when wood is immersed in water having worms, crustaceans such as barnacles, and the like, which tend to affix themselves to the wood. In addition, the composition exhibits antifungicidal properties. The composition can also be used to treat metallic articles or other objects which are subject to corrosion and fouling when exposed to ambient weather conditions or immersed in fresh or salt water.

DESCRIPTION OF PREFERRED EMBODIMENTS OF THE INVENTION

The composition comprises at least 25% by weight of a petrolatum wax having an oil content of at least about 10% and an effective amount of a biocidal compound or compounds. Preferably, the composition is 50% by weight wax, and most preferably in excess of 50% by weight wax and up to about 99% wax. Preferably, the oil content is in excess of 25% of the wax. A preferred example of a natural petrolatum from residual crude oil particularly adaptable to the present invention is Chevron Petrolatum 110 (also referred to as Chevron Unrefined Wax 110), a product of the Chevron U.S.A. Inc. company.

The petrolatum wax employed here is distinguished from other waxes by its semi-solid state at ordinary temperatures and its easy penetration and deformation under slight pressures. The congealing point of Chevron Petrolatum, the standard measure of petrolatum state change from solid to liquid, is 157° F. and may vary up to 2° F., measured by ASTM D-938. The penetration value, an empirical measure of the material's consistency, is 160 mm at 77° F., ASTM 937. Petrolatum are also distinguished by their high viscosity when melted; 165 @ 210° F. SUS, ASTM D-2161 for Chevron Petrolatum 110.

The low congealing point, high penetrability and viscosity of the petrolatum waxes allow them to be particularly adaptable for use in this invention. The combination of these properties results in a carrier medium which is very resistant to removal from an article or area once it has been supplied. The petrolatum wax is very viscous or sticky and will not chip or peel off as easily from the applied area as, for example, paraffinic waxes might. Petrolatum waxes are also more flexible and resilient than paraffinic waxes and better able to withstand high and low temperature thermocycling.

The structure of the wax is also such that it permits the timed release of the biocidal compound(s). This allows a relatively controlled amount of the biocide to be released over time, resulting in a longer compound effectiveness per application. Additionally, the cost of the petrolatum is relatively low in comparison to other carrier substances, an important consideration for quantity applications.

The biocidal compound is present in an amount of from 1 to 75% by weight of the composition. The biocidal compound can vary but preferred biocidal compounds are the oxides, salts, or hydrocarbyl compounds of copper, tin, nickel, zinc and mercury. Preferably, the metal is tin in the form of a hydrocarbyl tin oxide (organostannic) compound having a carbon atom content in the range of 1 to 20 and preferably 2 to 8 carbon atoms. Suitable organostannic compounds are dibutyl tin oxide, tributyl tin oxide, triisopropyloxostannic, bis(tributyltin)oxide, alkylphenoxytriethylstannic, and like compounds. The preferred range of dibutyl tin oxide is from about 1% to about 10% by weight and most preferably about 6% by weight. Derivatives of tin compounds such as salts, halogen, alkoxy, and aryl compounds are also suitable. The copper compounds can be copper oxide or copper naphthenate and like compounds. In addition, halogenated compounds such as pentachlorophenol and like compounds can be used as biocides.

The composition is formed by mixing the petrolatum wax at a temperature above its congealing point with an effective amount of the biocidal compound.

The article to be coated is dipped into the molten mixture. The number of dips determines the thickness of the coating. Two dips is approximately equal to one-eighth of an inch (3.2 mm), four dips equal one-fourth inch (6.2 mm) and every two additional dips are equal to one-fourth of an inch (6.2 mm). If the wooden article to be treated is dry and porous, the wax coating can be dipped or sprayed and the composition will be absorbed within the interior of the article to a depth depending upon the pore size and dryness of the article.

When the articles are exposed to salt water infested with barnacles, the non-aqueous composition of the present invention proves superior to paraffinic-based wax mixtures as well as a standard wood preservative such as pentachlorophenol.

Other ingredients in relatively minor amounts such as solvents, extenders and the like and the non-organic biocides can be incorporated into the mixture of the composition. However, the preferred composition is essentially a two-component non-aqueous composition of a major amount of petrolatum wax and a minor amount of a biocidal compound(s).

Having described the composition, the method of treating the articles and the treated articles, the following examples and comparative examples are provided to more clearly illustrate the invention but it is intended to be understood that the examples are not intended to limit the scope of the invention. Modifications which would be obvious to one of ordinary skill in the art are contemplated to be within the scope of the invention.

EXAMPLE 1

12,258 grams of Chevron Petrolatum 110 (now referred to as Chevron Unrefined Wax 110), a product of Chevron U.S.A. Inc., a natural petrolatum from crude oil wax having an oil content of about 40–45% by weight and a flash point of about 625° F. (329° C.) with a conjealing point of about 157° F. (69° C.) was mixed with 1362 grams of dibutyl tin oxide. The dibutyl tin oxide was present in an amount of about 1%. Kiln-dried Douglas Fir 2×4 boards about 30" long (5.08 cm×10.1 cm×76 cm) were dipped in the hot composition. The boards were dipped in the composition heated to about 180° F. (82° C.) two to eight times in multiples of two dips. After each pair of dippings, the coating was permitted to dry prior to additional coatings. Two dips was equivalent to about one-eighth of an inch in thickness (3.2 mm). Four dips resulted in a coating about one-fourth of an inch thick (6.4 mm). Six dips were about one-half inch thick (12 mm). Eight dips were about three quarter of an inch thick (19.2 mm). Finally, the coated wood was immersed in sea water and shielded from sunlight. Shielding the treated boards from sunlight was more severe test for rot and animal infestation and plant growth. The samples were inspected after two years for moss and sea barnacle growth as indicated in Table I hereinafter.

EXAMPLES 2 THROUGH 12

Various mixtures of Chevron Petrolatum Wax 110 and varying percentages of cuprous oxide or dibutyl tin oxide were mixed in accordance with the procedure outlined in Example I. Thereafter, the samples were immersed in sea water shielded from sunlight and inspected after two-years of immersion. Table I below indicates the results of the coatings for preserving the wood.

TABLE I

| Example | Treatment | Coating Thickness, No. of Dips | Sample Condition No Rotting of Any Sample | |
|---|---|---|---|---|
| | | | Sea Barnacles[1] | Moss[1] |
| 1 | 1% Dibutyl Tin Oxide[2] | 2 | VS | H |
| | | 4 | N | S |
| | | 6 | N | H |
| | | 8 | N | M |
| 2 | 2% Dibutyl Tin Oxide[2] | 2 | VS | M |
| | | 4 | N | M |
| | | 6 | N | H |
| | | 8 | N | M |
| 3 | 5% Dibutyl Tin Oxide[2] | 2 | N | M |
| | | 4 | N | S |
| | | 6 | N | M |
| | | 8 | N | S |
| 4 | 10% Dibutyl Tin Oxide[2] | 2 | N | S |
| | | 4 | N | S |
| | | 6 | N | S |
| | | 8 | N | S |
| 5 | 15% Dibutyl Tin Oxide[2] | 2 | N | S |
| | | 4 | N | S |
| | | 6 | N | N |
| | | 8 | N | N |
| 6 | 5% Cuprous Oxide[3] | 2 | S | S |
| | | 4 | S | S |
| | | 6 | N | M |
| | | 8 | N | S |
| 7 | 10% Cuprous Oxide[3] | 2 | S | S |
| | | 4 | S | S |
| | | 6 | S | M |
| | | 8 | S | S |
| 8 | 15% Cuprous Oxide[3] | 2 | S | H |
| | | 4 | N | M |
| | | 6 | VS | M |
| | | 8 | VS | M |
| 9 | 25% Cuprous Oxide[3] | 2 | M | M |
| | | 4 | S | M |
| | | 6 | VS | M |
| | | 8 | VS | M |
| 10 | 33% Cuprous Oxide[3] | 2 | S | S |
| | | 4 | N | M |
| | | 6 | N | M |
| | | 8 | N | M |
| 11 | 50% Cuprous Oxide[3] | 2 | S | H |
| | | 4 | S | M |
| | | 6 | VS | M |
| | | 8 | S | S |
| 12 | 75% Cuprous Oxide[3] | 2 | N | M |
| | | 4 | N | M |
| | | 6 | N | M |
| | | 8 | N | M |

[1]Code for amount of sea barnacles and moss: N equals none, VS equals very slight, S equals slight, M equals moderate, and H equals heavy.
[2]95% minimum active.
[3]100% minimum active.

Table I illustrates that the preferred range of dibutyl tin oxide was from 5% to 15% although it was satisfactory at 1% and 2% levels if the coatings were thicker i.e., ¼ to ½ inches thick (6.4 mm to 12.8 mm). Cuprous oxide was as effective as dibutyl tin oxide but only at higher concentrations, for example about 75%.

COMPARATIVE EXAMPLES

Air dry and kiln dry untreated Douglas Fir 2×4's were immersed in water. Kiln dry Douglas Fir 2×4's were coated with a commercial wood preservative (I), comprising about 46% of an aromatic solvent, about 5% of a Bunker Fuel Oil, about 28% of a cresylic acid, about 20% of a Chevron Base Oil and about 1% pentachlorophenol. Kiln dry Douglas Fir 2×4's were coated with another commercial wood preservative (II) comprising about 70% Chevron Weed Oil, 24.3% Base Oil and 5.7% pentachlorophenol. Several Douglas Fir 2×4's were coated with a Chevron Refined paraffin wax, Chevron Wax 154-156 AMP (now called Chevron Refined Wax 155), without biocide and refined paraffin wax, Chevron Wax 154-156 AMP, with 6% dibutyl tin oxide. In addition, several Douglas Fir 2×4's were coated with Chevron Petrolatum 110 wax and varying amounts of different biocides. The results of a three-year immersion of the samples are tabulated in Table II.

TABLE II

| | | Sample Condition | | | | | | | | |
|---|---|---|---|---|---|---|---|---|---|---|
| | | Protected from Sunlight | | | | | | In Sunlight | | |
| | | Extent of Rot | | | No. of Sea Barnacles | | | Extent of Rot | | Number of Sea Barnacles | |
| Ex. | Treatment[5] | 1st Yr. | 2nd Yr. | 3rd Yr. | 1st Yr. | 2nd Yr. | 3rd Yr. | 1st Yr. | 2nd Yr. | 1st Yr. | 2nd Yr. |
| 1 | Air dry Wood | f75% | 100% | 100% | Some | — | — | 50% | 50% | Some | Some |
| 2 | Kiln dry Wood | f75% | 100% | 100% | Some | — | — | 50% | 100% | Some | — |
| 3 | Wood Preservative (I) | 25% | 75% | 100% | Some | A lot | — | 25% | 25% | Some | Some |
| 4 | Wood Preservative (II) | 25% | 25% | 66% | Some | A Lot | — | 25% | 25% | Some | Some |
| | Refined Paraffin Wax with | | | | | | | | | | |
| 5 | (No Biocide) | 50% | 50% | 100% | Some | Some | — | 25% | 25% | Some | Some |
| 6 | (6% Dibutyl Tin Oxide) | 0% | 0% | 25% | None | None | None | 0% | 0% | None | None |
| | Chevron Petrolatum 110 with | | | | | | | | | | |
| 7 | (No biocide) | 50% | 50% | 100% | Some | Some | — | 50% | 50% | Some | Some |
| 8 | (40% Copper Naphthenate[1]) | 0% | 0% | 25% | Few | Few[4] | 50% | 0% | 0% | Few | Few |
| 9 | (5% Pentachlorophenol[2]) | 0% | 0% | 75% | Few | Few[4] | — | 0% | 0% | Very Few | Few[4] |
| 10 | (6% Dibutyl Tin Oxide[3]) | 0% | 0% | 0% | None | None | None | 0% | 0% | None | None |
| 11 | (75% Cuprous Oxide[2]) | 0% | 0% | 0% | None | None | None | 0% | 0% | None | None |

[1] 80% Active; 8% Copper
[2] 100% Active
[3] 95% Min. Active
[4] Only on the Side of the Board Facing Pier
[5] The samples were cracked and peeling The results indicate that the untreated wood and the wood treated with regular wood preservatives as well as with a refined parafinic wax containing a preferred amount of dibutyl tin oxide of the present invention showed various degrees of rotting from 25% to 100%. The petrolatum wax samples as outlined in Table II exhibited significantly and unexpectedly smaller amounts of barnacle growth and rotting.

The results clearly indicate that the non-aqueous compositions comprising a major amount of a petrolatum wax having a high oil content incorporating a biocide are unexpectedly superior to refined wax coatings and wood preservatives known in the art both to protect and extend the life of the wood and prevent the growth of barnacles.

What is claimed is:

1. A preservative composition which comprises at least about 25% by weight of a petrolatum wax having an oil content equal to or greater than about 10 weight percent of the wax and an effective amount of a biocide.

2. The composition according to claim 1 wherein the wax is present in an amount in excess of 25% of the composition.

3. The composition according to claim 2 wherein the wax is present in an amount in excess of 50%.

4. The composition according to claim 3 wherein the petrolatum wax has an oil content in excess of about 25 weight percent of the wax.

5. The composition according to claim 4 wherein the biocide is an oxide, salt, hydrocarbyl compound, halogenated hydrocarbyl compound or mixtures thereof containing a metallic element selected from the group of metals consisting of zinc, mercury, nickel, copper and tin.

6. The composition according to claim 5 wherein the biocide is a tin compound having a carbon atom content of from 1 to 20.

7. The composition according to claim 5 wherein the biocide is a tin compound.

8. The composition according to claim 7 wherein the tin compound is selected from the group consisting of dibutyl tin oxide, tributyl tin oxide, triisopropyloxostannic, and bis(tributyltin)oxide.

9. The composition according to claim 4 wherein the biocide is a halogenated hydrocarbyl compound.

10. An article treated with the composition according to claim 1 or 8.

11. A preservative composition which comprises at least about 50% by weight of a petrolatum wax having an oil content equal to or greater than about 25 weight percent of the wax and an effective amount of a biocide selected from the group consisting of dibutyl tin oxide, tributyl tin oxide, triisopropyloxastannic, and bis(tributyl tin) oxide.

12. The composition of claim 11 wherein the biocide is dibutyl tin oxide.

* * * * *